US006966649B2

(12) United States Patent
Shadduck

(10) Patent No.: US 6,966,649 B2
(45) Date of Patent: *Nov. 22, 2005

(54) ADAPTIVE OPTIC LENS SYSTEM AND METHOD OF USE

(76) Inventor: John H Shadduck, 1490 Vistazo West, Tiburon, CA (US) 94920

(*) Notice: Subject to any disclaimer, the term of this patent is extended or adjusted under 35 U.S.C. 154(b) by 52 days.

This patent is subject to a terminal disclaimer.

(21) Appl. No.: 10/639,894

(22) Filed: Aug. 12, 2003

(65) Prior Publication Data

US 2004/0100704 A1 May 27, 2004

Related U.S. Application Data

(63) Continuation-in-part of application No. 10/360,091, filed on Feb. 6, 2003, now Pat. No. 6,860,601.

(60) Provisional application No. 60/402,746, filed on Aug. 12, 2002.

(51) Int. Cl.[7] .............................. G02C 7/04; A61F 2/16
(52) U.S. Cl. ................. 351/177; 351/160 H; 351/177; 623/6.13; 623/6.22
(58) Field of Search ........................... 351/159, 160 R, 351/160 H, 161, 177; 623/6.13, 6.22

(56) References Cited

U.S. PATENT DOCUMENTS

| 4,253,199 A | 3/1981 | Banko |
| 4,373,218 A | 2/1983 | Schachar |
| 4,512,040 A | 4/1985 | McClure |
| 4,585,457 A | 4/1986 | Kalb |
| 4,685,921 A | 8/1987 | Peyman |
| 4,685,922 A | 8/1987 | Peyman |
| 4,693,717 A | 9/1987 | Michelson |
| 4,731,078 A | 3/1988 | Stoy et al. |
| 4,787,903 A | 11/1988 | Grendahl |
| 4,816,031 A | 3/1989 | Pfoff |
| 4,888,012 A | 12/1989 | Horn et al. |
| 4,892,543 A | 1/1990 | Turley |
| 4,902,293 A | 2/1990 | Feaster |
| 4,932,966 A | 6/1990 | Christie et al. |
| 4,950,289 A | 8/1990 | Krasner |
| 4,994,082 A | 2/1991 | Richards et al. |
| 5,035,710 A | 7/1991 | Nakada et al. |
| 5,066,301 A | 11/1991 | Wiley |
| 5,145,935 A | 9/1992 | Hayashi |
| 5,213,579 A | 5/1993 | Yamada et al. |
| 5,235,003 A | 8/1993 | Ward et al. |
| 5,275,623 A | 1/1994 | Sarfarazi |
| 5,288,293 A | 2/1994 | O'Donnell, Jr. |

(Continued)

FOREIGN PATENT DOCUMENTS

JP            9294754            11/1997

(Continued)

Primary Examiner—Scott J. Sugarman
(74) Attorney, Agent, or Firm—Nicola A. Pisano, Esq.; Luce, Forward, Hamilton & Scripps LLP

(57) ABSTRACT

An lens for correcting human vision, for example an IOL, contact lens or corneal inlay or onlay, that carries and interior phase or layer comprising a pattern of individual transparent adaptive displacement structures. In one embodiment, the displacement structures are actuated by a shape memory polymer (SMP) material or other polymer that is adjustable in shape in response to applied energy. The SMP can be designed to be selectively adjustable in volumetric dimension, modulus of elasticity and/or permeability. The adaptive optic means of the invention can be used to create highly localized surface corrections in the lens to correct higher order aberrations—which types of surfaces cannot be fabricated into and IOL and then implanted. The system of displacement structures also can provide spherical corrections in the lens.

20 Claims, 18 Drawing Sheets

U.S. PATENT DOCUMENTS

| | | |
|---|---|---|
| 5,443,506 A | 8/1995 | Garabet |
| 5,489,302 A | 2/1996 | Skottun |
| 5,506,300 A | 4/1996 | Ward et al. |
| 5,578,081 A | 11/1996 | McDonald |
| 5,665,822 A | 9/1997 | Bitler et al. |
| 5,774,273 A | 6/1998 | Bornhorst |
| 5,843,188 A | 12/1998 | McDonald |
| 5,984,962 A | 11/1999 | Anello et al. |
| 6,013,101 A | 1/2000 | Israel |
| 6,117,171 A | 9/2000 | Skottun |
| 6,124,980 A | 9/2000 | Cerbell |
| 6,188,526 B1 | 2/2001 | Sassaya et al. |
| 6,195,807 B1 | 3/2001 | Chou |
| 6,217,612 B1 | 4/2001 | Woods |
| 6,299,641 B1 | 10/2001 | Woods |
| 6,388,043 B1 | 5/2002 | Langer et al. |
| 6,450,642 B1 | 9/2002 | Jethmalani et al. |
| 6,493,151 B2 | 12/2002 | Schachar |
| 6,552,860 B1 | 4/2003 | Alden |
| 6,616,691 B1 | 9/2003 | Tran |
| 6,638,306 B2 | 10/2003 | Cumming |
| 6,645,245 B1 | 11/2003 | Preussner |
| 6,660,035 B1 | 12/2003 | Lang et al. |
| 6,692,525 B2 | 2/2004 | Brady et al. |
| 6,695,881 B2 | 2/2004 | Peng et al. |
| 6,709,108 B2 * | 3/2004 | Levine et al. ............... 351/211 |
| 6,712,848 B1 | 3/2004 | Wolf et al. |
| 6,721,043 B2 * | 4/2004 | Platt et al. .................. 356/124 |
| 6,730,123 B1 | 5/2004 | Klopotek |
| 6,749,632 B2 | 6/2004 | Sandstedt et al. |
| 2001/0016771 A1 | 8/2001 | Cumming |
| 2003/0003295 A1 | 1/2003 | Dreher et al. |
| 2003/0050695 A1 | 3/2003 | Lin et al. |
| 2003/0060878 A1 | 3/2003 | Shadduck |
| 2003/0149480 A1 | 8/2003 | Shadduck |
| 2004/0001180 A1 | 1/2004 | Epstein |
| 2004/0006387 A1 | 1/2004 | Kelman |
| 2004/0008419 A1 | 1/2004 | Schachar |
| 2004/0015236 A1 | 1/2004 | Sarfarazi |
| 2004/0039446 A1 | 2/2004 | McNicholas |
| 2004/0054408 A1 | 3/2004 | Glick et al. |
| 2004/0082994 A1 | 4/2004 | Woods et al. |
| 2004/0085511 A1 | 5/2004 | Uno et al. |
| 2004/0111151 A1 | 6/2004 | Paul et al. |
| 2004/0111152 A1 | 6/2004 | Kelman |
| 2004/0127984 A1 | 7/2004 | Paul et al. |
| 2004/0162612 A1 | 8/2004 | Portney et al. |
| 2004/0181279 A1 | 9/2004 | Nun |

FOREIGN PATENT DOCUMENTS

| | | |
|---|---|---|
| JP | 11276509 | 10/1999 |
| WO | WO0041650 | 7/2000 |
| WO | WO0197742 | 12/2001 |
| WO | WO 2004/010895 | 2/2004 |

* cited by examiner

ADAPTIVE OPTIC LENS SYSTEM AND METHOD OF USE

CROSS-REFERENCE TO RELATED APPLICATIONS

This application claims benefit under 35 U.S.C. § 119(e) of Provisional U.S. Patent Applications: Ser. No. 60/402,746 filed Aug. 12, 2002 titled Intraocular Lens Implant. This application also is a Continuation-In-Part of U.S. patent application Ser. No. 10/360,091 filed Feb. 6, 2003, U.S. Pat. No. 6,860,601 titled Adapive Optic Lens System and Method of Use. Both of the above applications are incorporated herein by this reference.

BACKGROUND OF THE INVENTION

1. Field of the Invention

The present invention pertains to an ophthalmic lens that allows for post-fabrication correction of higher order aberrations or spherical corrections. More in particular, the invention can be used in IOLs and contact lenses wherein lens components respond to an external energy source, such as a laser, to allow adaptive structures in an interior lens phase to be altered in dimension to thereby adjust or flex the lens shape in a manner akin to methods used in the field of adaptive optics (AO) in astronomical telescopes for higher order wavefront corrections.

2. Description of the Related Art

Post-fabrication adjustment of optical characteristics of lenses is needed in various ophthalmic lens types. In one case, cataract patients would benefit from post-implant power adjustability of an IOL implant. In another case, posterior chamber phakic IOLs could benefit from post-implant power adjustability since biometry cannot insure proper power selection. Also, contact lenses would benefit from post-fabrication curvature adjustment to limit the number of lenses that needed to be maintained in inventories.

Cataracts are major cause of blindness in the world and the most prevalent ocular disease. Visual disability from cataracts accounts for more than 8 million physician office visits per year. When the disability from cataracts affects or alters an individual's activities of daily living, surgical lens removal with intraocular lens implantation is the preferred method of treating the functional limitations. In the United States, about 2.5 million cataract surgical procedures are performed annually, making it the most common surgery for Americans over the age of 65. About 97 percent of cataract surgery patients receive intraocular lens implants, with the annual costs for cataract surgery and associated care in the United States being upwards of $4 billion.

A cataract is any opacity of a patient's lens, whether it is a localized opacity or a diffuse general loss of transparency. To be clinically significant, however, the cataract must cause a significant reduction in visual acuity or a functional impairment. A cataract occurs as a result of aging or secondary to hereditary factors, trauma, inflammation, metabolic or nutritional disorders, or radiation. Age-related cataract conditions are the most common.

In treating a cataract, the surgeon removes material from the lens capsule and replaces it with an intraocular lens (IOL) implant. The typical IOL provides a selected focal length that allows the patient to have fairly good distance vision. Since the lens can no longer accommodate, the patient typically needs prescription eyeglasses for reading. The surgeon selects the power of the IOL based on analysis of biometry of the patient's eye prior to the surgery.

In a significant number or cases, after the patient's eye has healed from the cataract surgery, there is a refractive error was beyond the margin of error in the biometric systems. Thus, there remain intractable problems in calculating the proper power of an IOL for any particular patient. To solve any unpredicted refractive errors following IOL implantation, the ophthalmologist can perform a repeat surgery to replace the IOL—or the patient can live with the refractive error and may require prescription eyeglasses to correct for both near and distant vision.

What is needed is a lens system that provides means for post-fabrication or post-implant adjustment of optical characteristics and dioptic power. What also is needed is a lens system that can correct higher order aberrations.

SUMMARY OF THE INVENTION

Of particular interest, the lens corresponding to the invention falls into the class of adaptive optics (AO) in the sense that micro-scale actuator means are provided to flex and alter the curvature of the lens surface locally for higher order aberrations or globally for spherical corrections, within a selected range of dimensions. The usual scope of the AO field encompasses flex-surface mirrors wherein piezoelectric or other drivers can flex the optical surface within microsecond intervals to reduce aberrations, for example in astronomical telescopes as shown in FIG. 1A. The actuators of the present invention differ completely in that they only need be actuated one time, or perhaps a few times, and there is no need for rapid actuation response times. Still the invention provides an AO structure wherein the adaptive optics comprise soft actuators at a micro-scale suitable for correcting higher order aberrations disposed in an interior of the lens. The actuators are transparent with an index that matches the material of lens body, as indicated schematically in FIG. 1B. In one preferred embodiment, the adaptive structure is responsive to localized energy application thereto, preferably in the form of light energy. A light source operating in the 400 nm to 1.4 micron range is suitable (not limiting) which will typically comprise a laser but other non-laser light sources fall within the scope of the invention. The light source is coupled to a computer controller, galvanometric scanner (or any other type of scanner), and optional eye-tracking system, all of which are known in the art (e.g., in LASIK systems) and for this reason need no further description for adjusting an IOL. The micro-actuator means, or more particularly the soft adaptive structures are indicated in FIG. 1B, and comprise a plurality of displacement structures that define selected micron scale dimensions across principal and secondary axes thereof, wherein the structures engage at least one deformable lens surface layer. In a contact lens, the light source can be less complex and need not be scanned as will be described below.

BRIEF DESCRIPTION OF THE DRAWINGS

In order to better understand the invention and to see how it may be carried out in practice, some preferred embodiments are next described, by way of non-limiting examples only, with reference to the accompanying drawings, in which.

DETAILED DESCRIPTION OF THE PREFERRED EMBODIMENTS

Figure 1A:
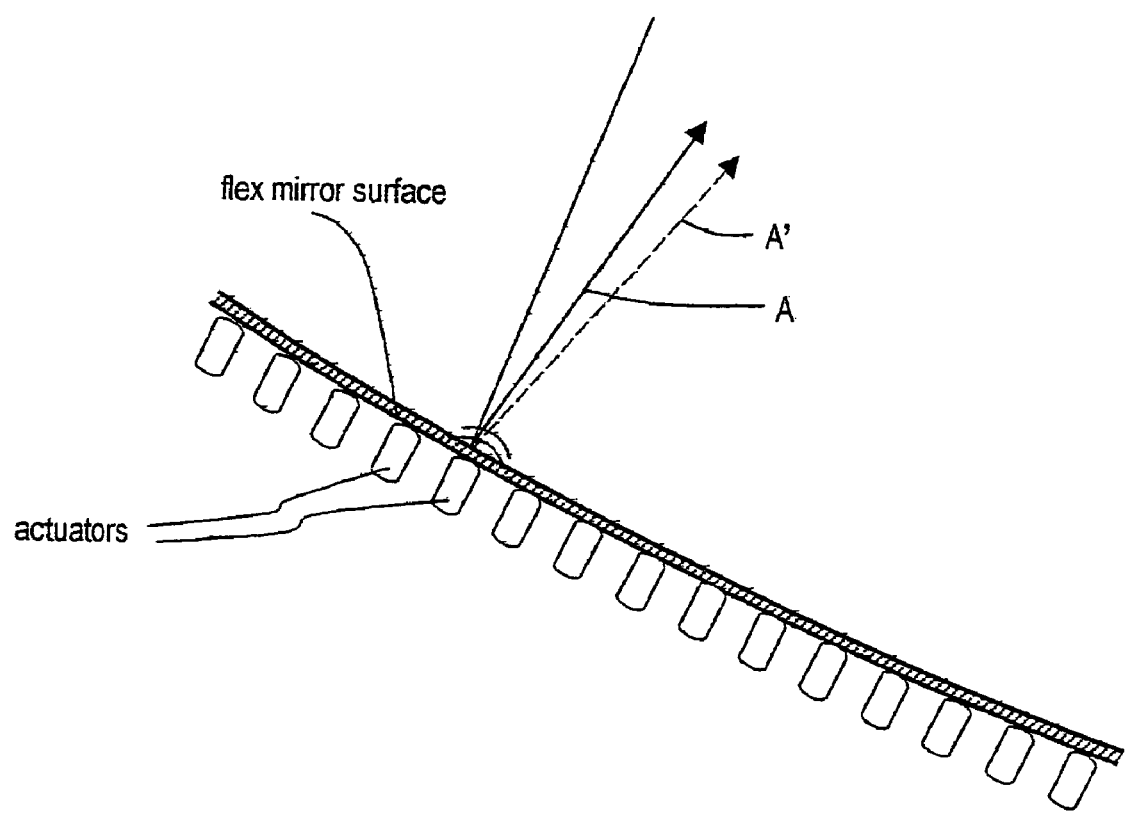
FIG. 1A is conceptual view of AO (adaptive optics) as known in the art of deformable mirrors for astronomical telescopes with actuators at an exterior of the reflective mirror plane.

I. Principles of Shape Memory in Polymers for Use in Adaptive Lenses

Several alternative embodiments of the invention utilize a shape memory polymer (SMP) to enable the transparent index-matched actuator system corresponding to the invention. For this reason, a background on shape memory polymers is provided.

Shape memory polymers demonstrate the phenomena of shape memory based on fabricating a segregated linear block co-polymer, typically of a hard segment and a soft segment. The shape memory polymer generally is characterized as defining phases that result from glass transition temperatures in the hard and a soft segments. The hard segment of SMP typically is crystalline with a defined melting point, and the soft segment is typically amorphous, with another defined transition temperature. In some embodiments, these characteristics may be reversed together with the segment's glass transition temperatures.

In one embodiment, when the SMP material is elevated in temperature above the melting point or glass transition temperature $T_g$ of the hard segment, the material then can be formed into a memory shape. The selected shape is memorized by cooling the SMP below the melting point or glass transition temperature of the hard segment. When the shaped SMP is cooled below the melting point or glass transition temperature of the soft segment while the shape is deformed, that temporary shape is fixed. The original shape is recovered by heating the material above the melting point or glass transition temperature of the soft segment but below the melting point or glass transition temperature of the hard segment. (Other methods for setting temporary and memory shapes are known which are described in the literature below). The recovery of the original memory shape is thus induced by an increase in temperature, and is termed the thermal shape memory effect of the polymer. The temperature can be body temperature or another selected temperature above 37° C. for the present invention.

Besides utilizing the thermal shape memory effect of the polymer, the memorized physical properties of the SMP can be controlled by its change in temperature or stress, particularly in ranges of the melting point or glass transition temperature of the soft segment of the polymer, e.g., the elastic modulus, hardness, flexibility, permeability and index of refraction. The scope of the invention of using SMPs in IOLs extends to the control of such physical properties.

Examples of polymers that have been utilized in hard and soft segments of SMPs include polyurethanes, polynorborenes, styrene-butadiene co-polymers, cross-linked polyethylenes, cross-linked polycyclooctenes, polyethers, polyacrylates, polyamides, polysiloxanes, polyether amides, polyether esters, and urethane-butadiene co-polymers and others identified in the following patents and publications: U.S. Pat. No. 5,145,935 to Hayashi; U.S. Pat. No. 5,506,300 to Ward et al.; U.S. Pat. No. 5,665,822 to Bitler et al.; and U.S. Pat. No. 6,388,043 to Langer et al. (all of which are incorporated herein by reference); Lui et al., *Thermomechanical Characterization of a Tailored Series of Shape Memory Polymers*, J. App. Med. Plastics, Fall 2002; Gorden, *Applications of Shape Memory Polyurethanes*, Proceedings of the First International Conference on Shape Memory and Superelastic Technologies, SMST International Committee, pp. 115–19 (1994); Kim, et al., *Polyurethanes having shape memory effect*, Polymer 37(26):5781–93 (1996); Li et al., *Crystallinity and morphology of segmented polyurethanes with different soft-segment length*, J. Applied Polymer 62:631–38 (1996); Takahashi et al., *Structure and properties of shape-memory polyurethane block copolymers*, J. Applied Polymer Science 60:1061–69 (1996); Tobushi H., et al., *Thermomechanical properties of shape memory polymers of polyurethane series and their applications*, J. Physique IV (Colloque C1) 6:377–84 (1996)) (all of the cited literature incorporated herein by this reference).

Shape memory polymers foams within the scope of the invention typically are polyurethane-based thermoplastics that can be engineered with a wide range of glass transition temperatures. These SMP foams possess several potential advantages for intraocular implants, for example: very large shape recovery strains are achievable, e.g., a substantially large reversible reduction of the Young's Modulus in the material's rubbery state; the material's ability to undergo reversible inelastic strains of greater than 10%, and preferably greater that 20% (and up to about 200%–400%); shape recovery can be designed at a selected temperature between about 30° C. and 45° C. which may be useful for the implants; and injection molding is possible thus allowing complex shapes. As described above, these polymers also demonstrate unique properties in terms of capacity to alter the material's water or fluid permeability, thermal expansivity, and index of refraction. However, the material's reversible inelastic strain capabilities leads to its most important property—the shape memory effect. If the polymer is strained into a new shape at a high temperature (above the glass transition temperature $T_g$) and then cooled it becomes fixed into the new temporary shape. The initial memory shape can be recovered by reheating the foam above its $T_g$.

II. Exemplary Lens that Utilizes Transparent Interior Displacement Structures

1. Type "A" Soft Adaptive Optic System.

The adaptive optic system of the invention can be used in an ophthalmic lens, such as an IOL (intraocular lens) or a contact lens to allow for post-fabrication power adjustment or post-implant adjustment. For purposes of explanation, the principles of the invention are first shown in FIG. 2 in an intraocular lens 100 for cataract treatment, but also can be for any phakic IOL for the anterior chamber of posterior chamber.

Figure 2:
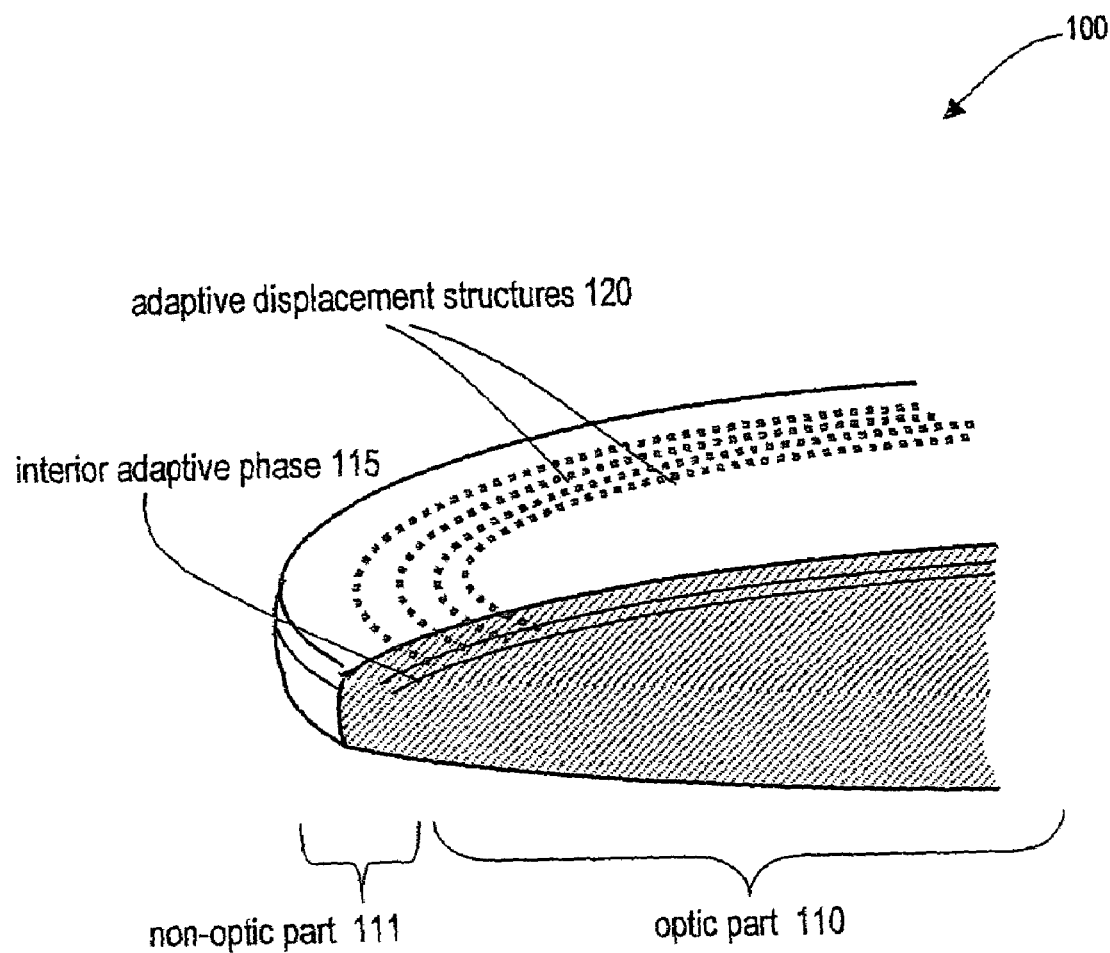
FIG. 2 is a schematic perspective cut-away view of a portion of a Type "A" intraocular lens (IOL) with an interior plane or phase carrying an AO (adaptive optics) structure corresponding to the invention.
Figure 3:
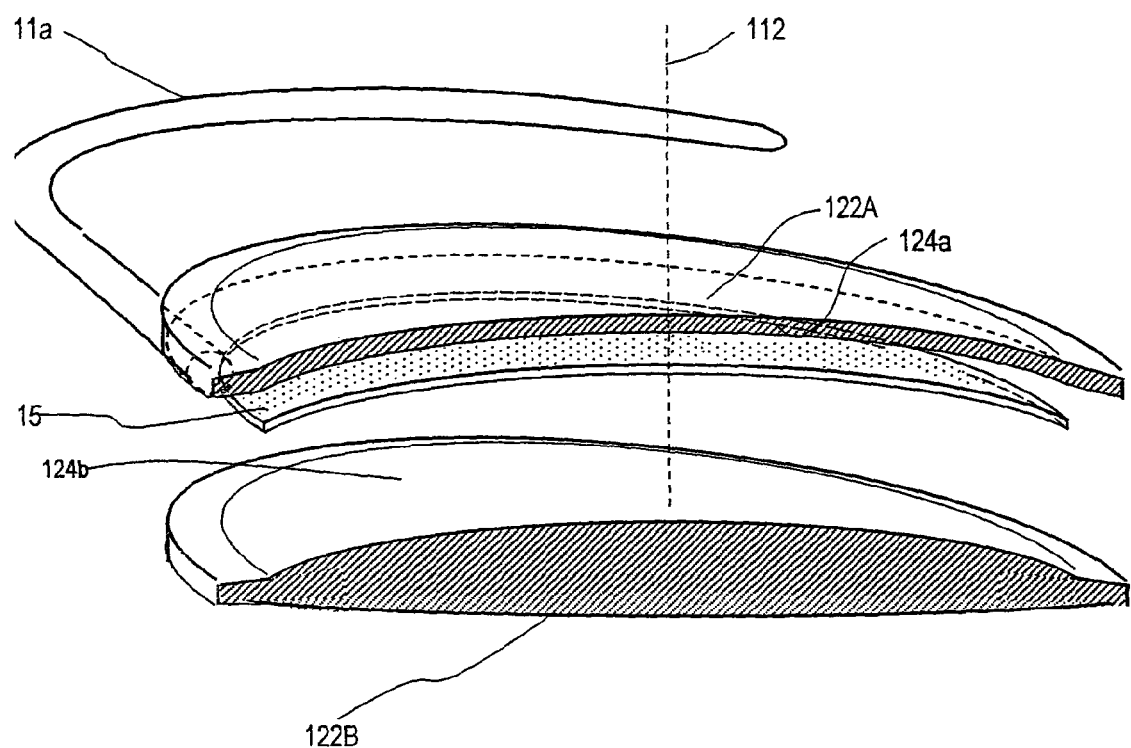
FIG. 3 is a sectional view of the IOL of FIG. 2 with the lens components de-mated to illustrate the method of fabricating an adaptive optic IOL or contact lens.

In FIGS. 2 and 3, the IOL 100 defines an optic part 110 and non-optic part 111 (or haptic) wherein the lens defines an optical axis 112 and has an interior phase 115 that carries a pattern of adaptive optic structures or displacement structures 120 therein for adjusting the optical power of the lens. The non-optic portions 111 defines an optic periphery 114 in a radially outward part of body lens body 118 that transitions to any type of loop haptics or plate haptics, with one haptic indicated at 111a in FIG. 3, as is known in the art. The lens typically would range from about 4.5 mm to 6.5 mm in diameter (not limiting) of an IOL with different dimensions for inlays (e.g., 3.0 to 5.0 mm. in diameter or contact lenses.

As can be seen in FIG. 2, the optic portion 110 defines a first anterior lens surface 122A and a second posterior lens surface 122B that extend toward the optic periphery 114. The first and second polymer body portions or layers 124a and 124b that define the anterior and posterior surfaces 122A and 122B, respectively, are substantially fluid impermeable transparent polymers with any suitable refractive index as is known in the art. In this embodiment, the first and second polymer layers 124a and 124b envelope the interior phase 115 that carries a patterned displacement structures 120. Each displacement structures 120 has an index of refraction that matches body portions or layers 124a and 124b. The anterior surface layer 124a of the lens is deformable by application of forces by each displacement structure 120 or any collective number of structures or actuators after actuation from a first stable volume or shape to a second volume or shape. Of particular interest, the displacement structures 120 define a micro-scale that makes the system suitable for correcting higher order aberrations. The lens carries from about 20 to 1000 displacement structures 120, and more preferably carries from about 25 to 125 such displacement structures 120 in any fixed pattern such as each structure 120 having a center about set of concentric circles about the lens axis 115. The structures 120 can be designed with similar or different amplitudes of adjustment for different strategies in post-implant correction.

The scope of the invention includes displacement structures 120 of a transparent shape change material, any material that changes density or porosity in a fluid environment, or any displaceable media such as a fluid or gel that is moved or pressurized In other words, the displacement structures comprise media that is adjustable from a first stable functional parameter to a second stable parameter in response to energy applied to a subpattern of locations on the lens body to individually alter each displacement structures 120, the functional parameters being in the class consisting of media volume, media shape, media porosity, media density and the media's internal pressure. As will be described below, the preferred method of applying energy to the lens body is the use of a laser.

Figure 4:
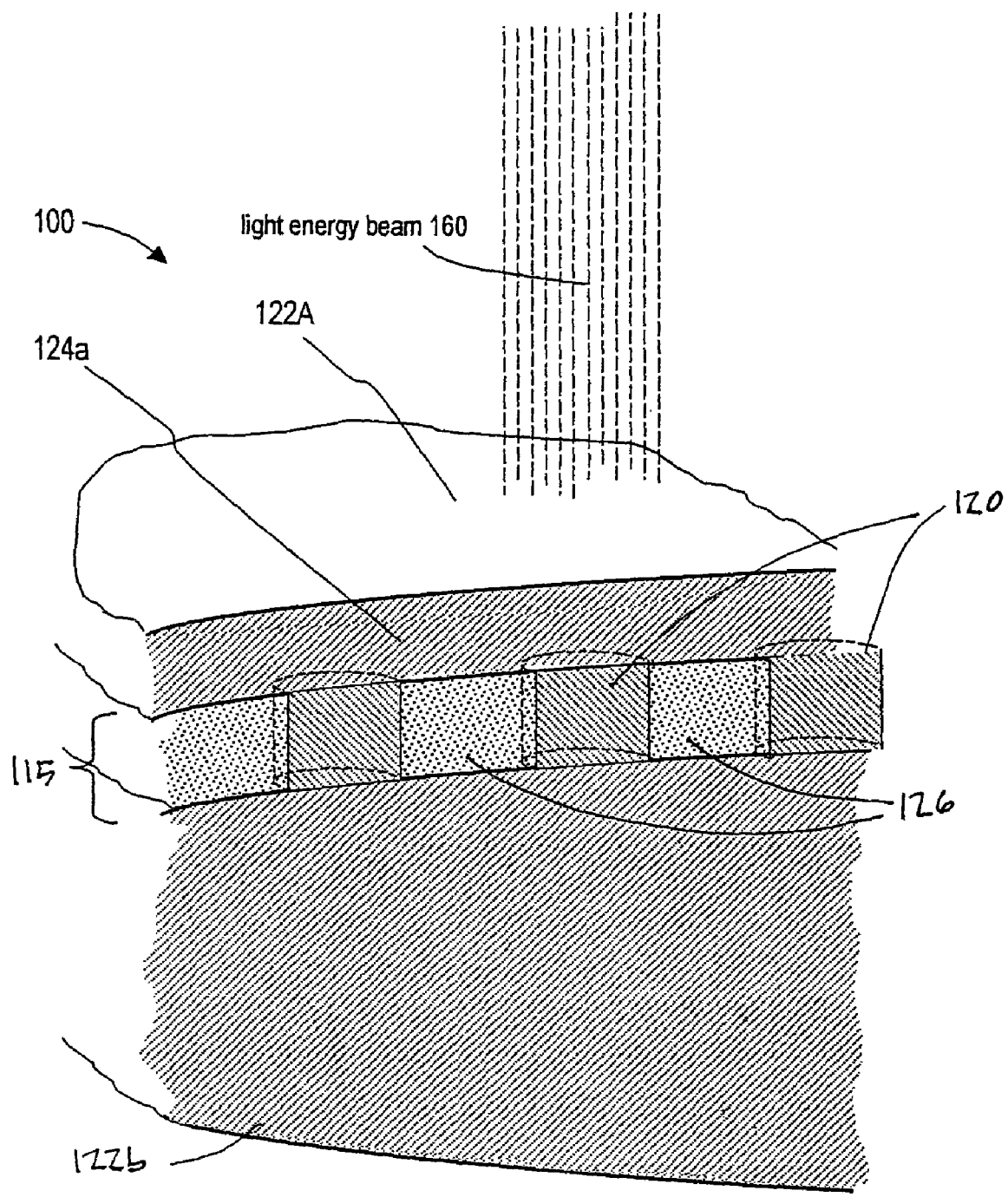
FIG. 4 is an enlarged view of a portion of the IOL of FIG. 3 that better illustrates the AO structure and the soft polymer displacement structures of a shape memory polymer.
Figure 5A:
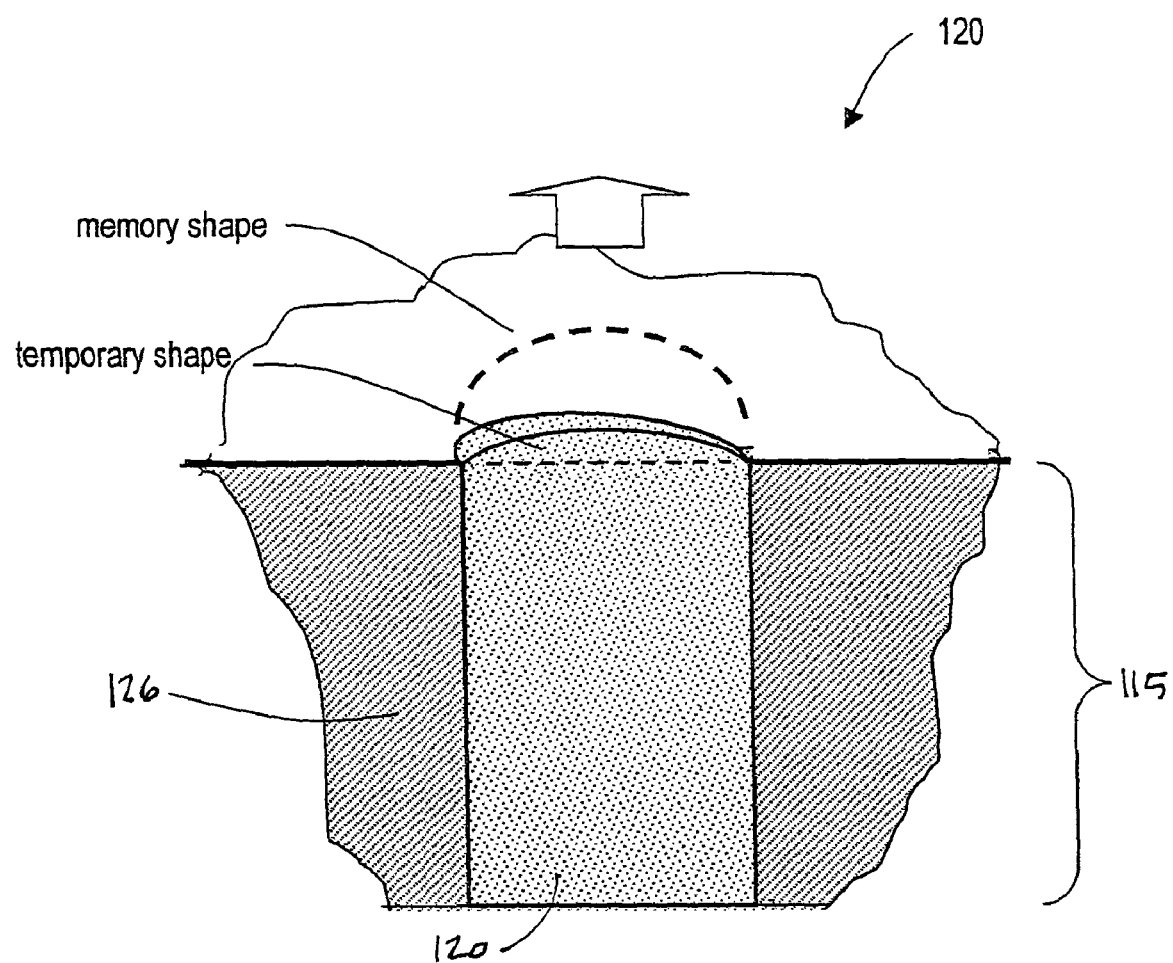
FIG. 5A is a greatly enlarged view of a soft actuator of FIG. 4 that shows the operation of the displacement structure wherein its dimensions are altered to ratably change between a temporary shape and a memory shape in response to localized light energy application.
Figure 5B:
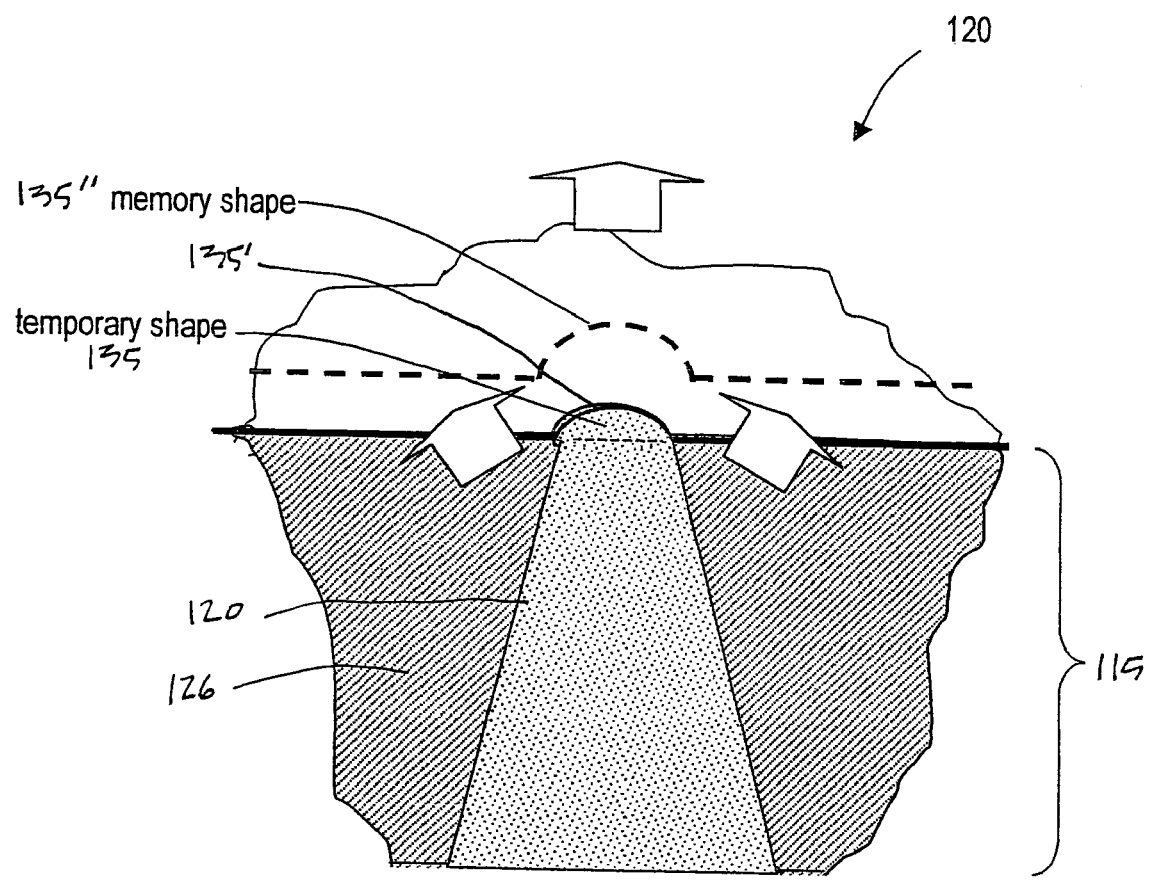
FIG. 5B is an enlarged view of a soft actuator similar to that of FIG. 5A that is adapted for either more local or more global shape changes depending on the level of applied energy.

In one embodiment, referring to FIGS. 3 and 4, the displacement structures or actuators 120 are shape memory polymer actuators, of any SMP materials described above or in the literature identified above. The anterior lens layer 124a defines a selected thickness dimension D and modulus of elasticity (E) that cooperates with the surface area A of the soft actuator 120 to insure that the radius of curvature in the deformed layer 124a is within selected parameters. The thickness dimension D of the deformable anterior layer 124a is from about 1 micron to 100 microns. More preferably, the dimension D of anterior layer 124a is from about 5 microns to 50 microns. Referring to FIGS. 5A and 5B, an exemplary displacement structure 120 can take on any cylindrical or other form in its temporary shape and provide a surface area A of at least about 5 sq. microns and preferably at least about 20 sq. microns. Referring to FIGS. 2 and 3, the first and second polymer portions 124a and 124b envelope the interior phase or plane 115 that consists of the displacement structures 120 and an intermediate media 126 that is a very low modulus index-matched material, an indexed-matched gel or a porous structure with an index-matched fluid media 140 therein. In these exemplary embodiments, the intermediate media or phase portion 126 is adapted to occupy the lens volume and provide stable refraction before and after adjustment lens with actuation of the displacement structures 120. In the embodiments that utilize a fluid media 140 therein, a silicone of a selected viscosity can be used. Silicone fluids are linear polymers whose chains contain between 2 and well over 1,000 silicon atoms, each of which is linked to the next by an oxygen atom. Together, these materials join to form what we know as a polydimethylsiloxane. Of particular interest for the invention, silicone fluids can be fabricated to provide the matching index of refraction as described above. Silicones change very little in viscosity over a wide temperature range, which together with their high wetting power can will provide the properties needed for the functioning of the adaptive structure of lens corresponding to the invention. Further, silicones fluids are inherently inert towards the other substrates that are anticipated to be used in the invention. All these characteristics, low viscosity change vs. temperature, dielectric stability, chemical inertness, shear stability, low surface tension, oxidative stability, thermal stability and high compressibility make silicone a logical candidate for use in the invention.

Further, it is believed that silicone fluids, in this application, will be found to be a biocompatible material for the interior of a lens implant following FDA regulatory reviews.

The viscosity of silicones is typically measured in units called centistokes (cSt) wherein the lower the number, the thinner and less viscous the material. A silicone fluid 140 for use in the lens can have a viscosity ranging from about 0.65 cSt to about 1,000,000 cSt, which ranges from a very low viscosity fluid upward to a high viscosity fluid. More preferably, the silicone fluid 140 can have a fluid viscosity ranging from about 5.0 cSt to 100,000 cSt, which at the upper range resembles a slow moving gel. More preferably, a silicone fluid 140 can have a fluid viscosity ranging from about 10 cSt to 5,000 cSt. A wide number of commercial sources of silicone fluids are known, for example, NuSil Silicone Technology, Inc. (www.nusil.com); General Electric, Inc. (www.gesilicones.com) and Dow Corning, Inc. (www.dowcorning.com). While silicone fluid is a preferred material for use in the invention, it should be appreciated that hydrogels and any other fluids fall with suitable matching indices, viscosities and biocompatibility fall within the scope of the invention. The fluid 140 is provided in the interior phase 115 by post-assembly fluid injection, or by fluid-immersion assembly means as is known in the art.

Figure 1B:
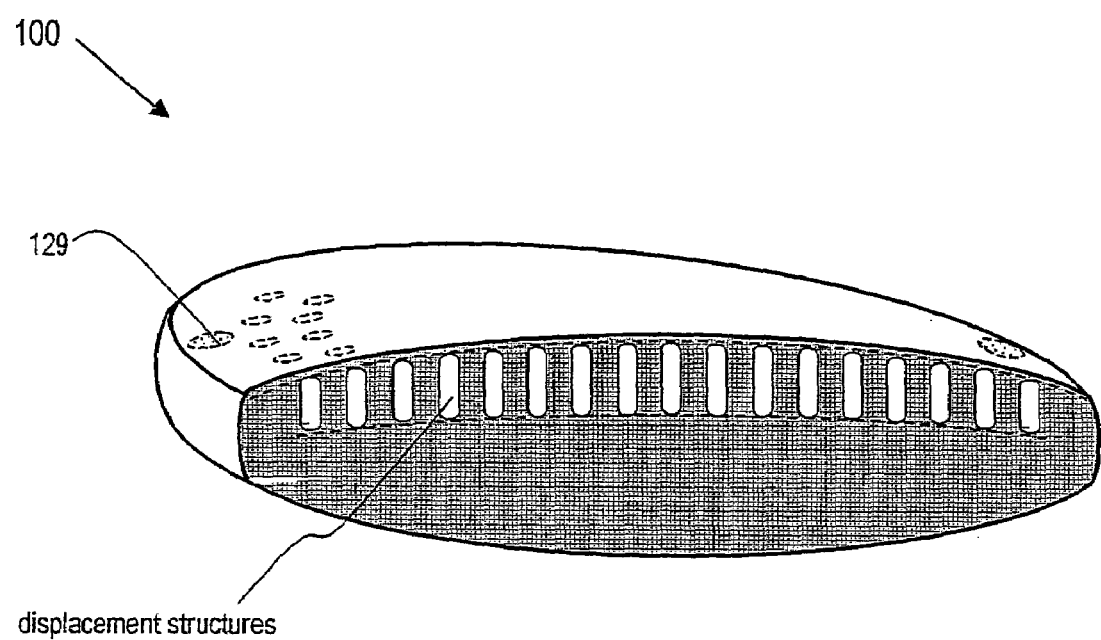
FIG. 1B is a conceptual representation of a lens element, for example and IOL or contact lens with, including transparent index-matched soft polymer displacement structures or actuators at an interior plane of the lens in one embodiment of the AO (adaptive optics) structure corresponding to the invention.

The exemplary lens of FIGS. 2 and 3 is bi-convex, but the invention can be extended to plano-convex, concavo-convex lens or any other type of lens or DOE (diffraction optical element), for example that utilize kinoforms or binary optics, or the invention can be extended to thin film diffractive optics. In one embodiment, referring to FIGS. 1B and 2, the lens surface and each adaptive element or portion is assigned an address indicated at 127 (collectively). By the term address, it is meant that the spatial location of the lenticular surface overlying the adaptive element is assigned surface coordinates in relation to reference markers indicated at 129. The reference markers 129 may be singular or plural and located anywhere in the lens, but are most likely in a peripheral region. The reference points are utilized to allow the light source and its computer-controlled scanning system to assign addresses 127 to the locations of the adaptive structures (see FIG. 1B). The reference markers typically would function based on reflectivity with a reference light beam and sensing system similar to that used in a CD (compact disc), which is known in the art and need not be described further. While typically, the spaced apart adaptive structures 120 are arranged in concentric circles within the lens, the structures also can be in any fixed pattern such as a spiral pattern, or in a grid. While the shape recoverable polymer elements of FIG. 1B are generally described herein for convenience as being adapted to change shape and to thereby push the anterior surface 124a (FIG. 3) outwardly, it should be appreciated that the shape recoverable elements can extend substantially axially through the lens body (FIG. 1B), or orthogonal to the lens axis and pull or tension the lens surface inwardly.

In another embodiment described below, it should be appreciated that the scope of the invention includes a deformable anterior layer 124a that is a surface treatments or surface modifications of a polymeric actuator layer 115 rather than a discrete layer of a bonded-on additional layer. Such surface treatments can be accomplished to provide substantially uniform thicknesses D as described immediately above. See for example, U.S. Pat. No. 5,235,003 to R. Ward et al, which is incorporated herein by reference together with other patents by R. Ward claiming benefit of, or connection to, this patent that related to the creation of polymer surface modifications.

In exemplary embodiment illustrated in FIGS. 2 and 3, the materials 124a and 124b that provide the surface layers around the interior phase 115 are of a resilient polymeric material with a selected thickness and deformation characteristics, and can be a silicone, hydrophilic acrylic polymeric material, hydrophobic acrylic material, hydrogel material, collamer or the like, all of which are known in the art IOL fabrication. This material preferably has an index of refraction above about 1.40. More preferably, the index of refraction is above about 1.45. These materials will allow the lens to be folded or rolled for carrying in a small cross-section introducer device for deployment into the eye through a small incision. As will be described below, the functionality of the lens depends on the resilient characteristic of at least one lens surface layer. The lens body, or at least one surface layer, also can be fabricated of a slightly stiffer biocompatible material if very thin in cross section, such as polymethyl methacrylate (PMMA). Thus, it is possible that the lens material layers can be formed of different materials, such as one silicone layer and one PMMA layer. The material layers, depending on the material, can be injection-molded, or fabricated with cast or compression molding techniques or turned by a lathe as is known in the art, including the adaptive structures described below.

The SMP of the displacement structures 120 have a selected $T_g$ (as described above) at which the actuator will move toward its memory shape (see FIG. 5A) to thereby impinge on surface 124a of layer 122A to alter the optical characteristics of the lens 100. FIG. 4 shows a method of the invention wherein light energy is applied to a single displacement structure 120 to alter it shape axially and deform the surface layer 124 to correct an aberration. The light energy in scanned and tracked as is known in the art, and intraoperative wavefront diagnostics can be used to during energy delivery. It is believed that nomograms can be developed so that the SMP of the displacement structures 120 can be gradually changed to provide a plurality of stable actuation positions between its temporary shape and memory shape. The selected $T_g$ is any selected temperature above body temperature which can be achieved by irradiation of the displacement structures 120 with a selected light wavelength. The selected $T_g$ of the SMP of each structure 120 can be in the range of about 40° C. to about 80° C. More preferably, the selected $T_g$ of the SMP is in the range of about 42° C. to about 70° C. Still more preferably, the selected $T_g$ of the SMP is in the range of about 42° C. to about 55° C. The SMP can carry any suitable chromophore to cooperate with a selected wavelength that can range from the UV to the infrared. It should be appreciated that the soft actuator can comprise a two-way shape memory material as described above to thereby provide two memory shapes.

FIG. 5B shows a similar soft SMP member that can adjust and displace and surface layer for both locally and more global shape changes. The actuator's temporary shape at its anterior surface is indicated at 135. Upon a first level of applied energy, the SMP is altered to 135' to locally adjust a surface layer 124a (not shown). Upon a second level of applied energy, the SMP is altered to 135" to globally adjust surface layer 124a wherein all of layer 115 is adaptive.

Figure 6A:
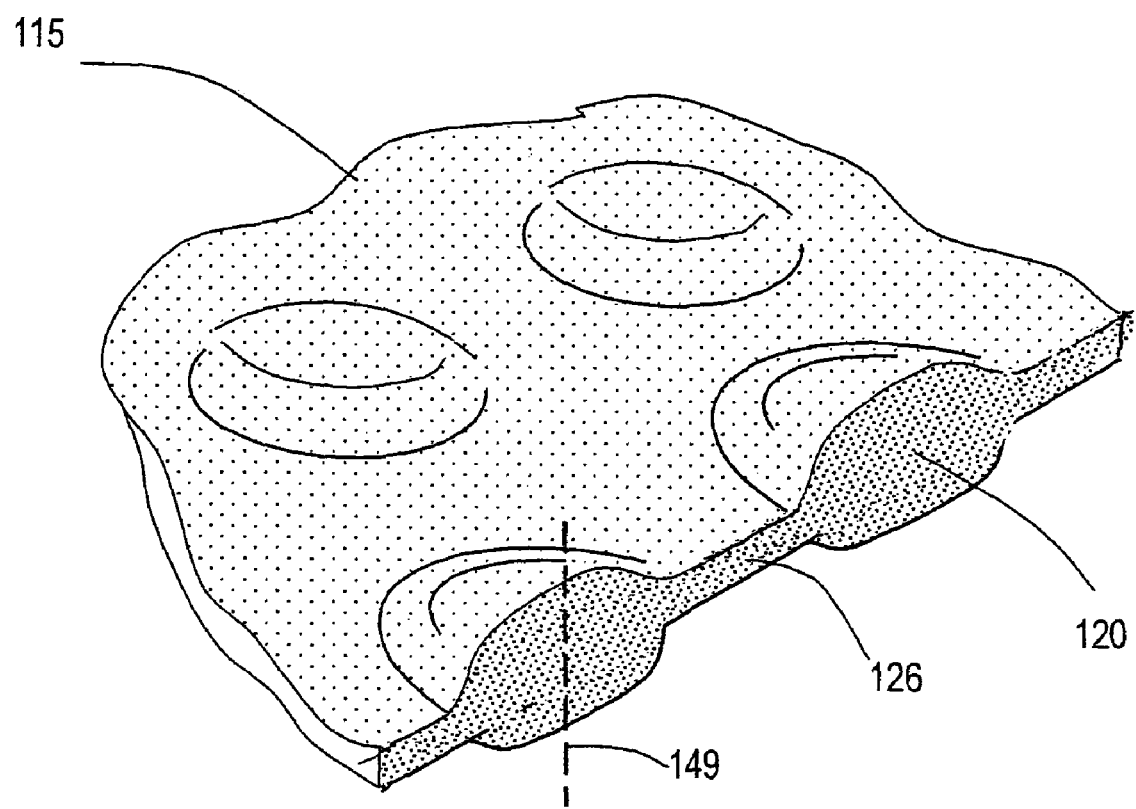
FIG. 6A is a sectional view of a portion of an interior phase of a lens that carries the adaptive displacement structures in its molded memory shape, and its method of making.
Figure 6B:
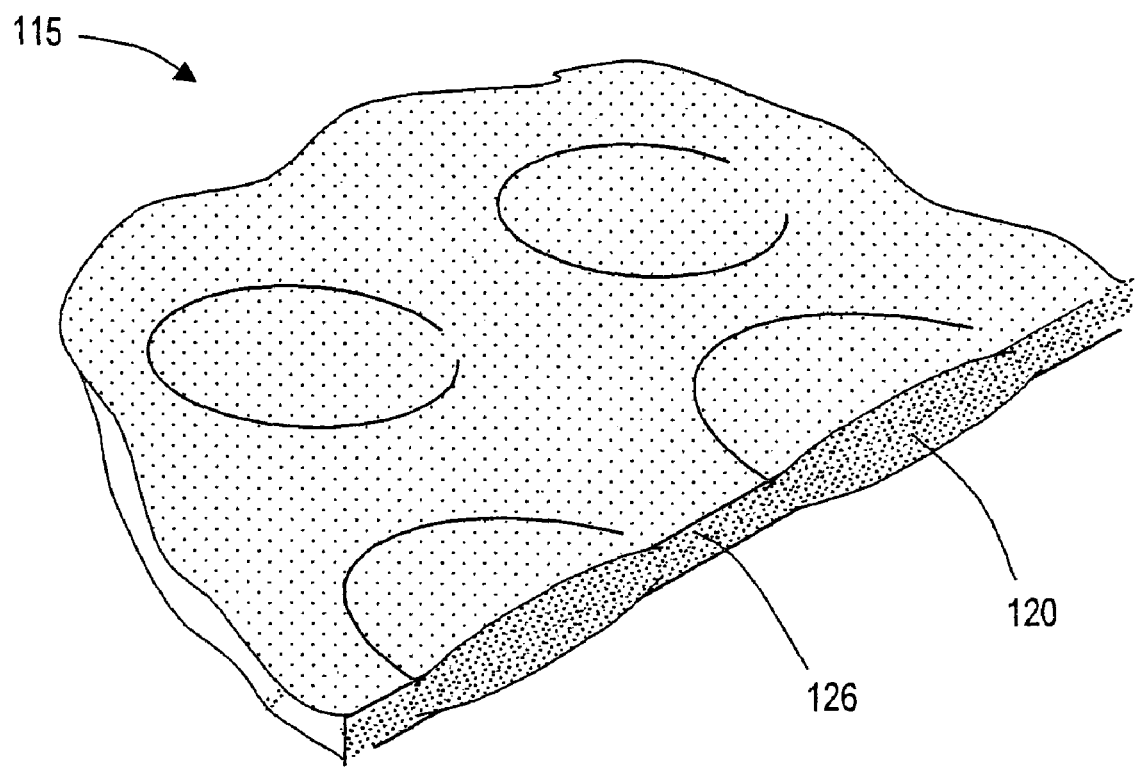
FIG. 6B is a sectional view of the interior phase portion of FIG. 6A with the adaptive displacement structures secondarily molded into the SMP's stable temporary shape.
Figure 6C:
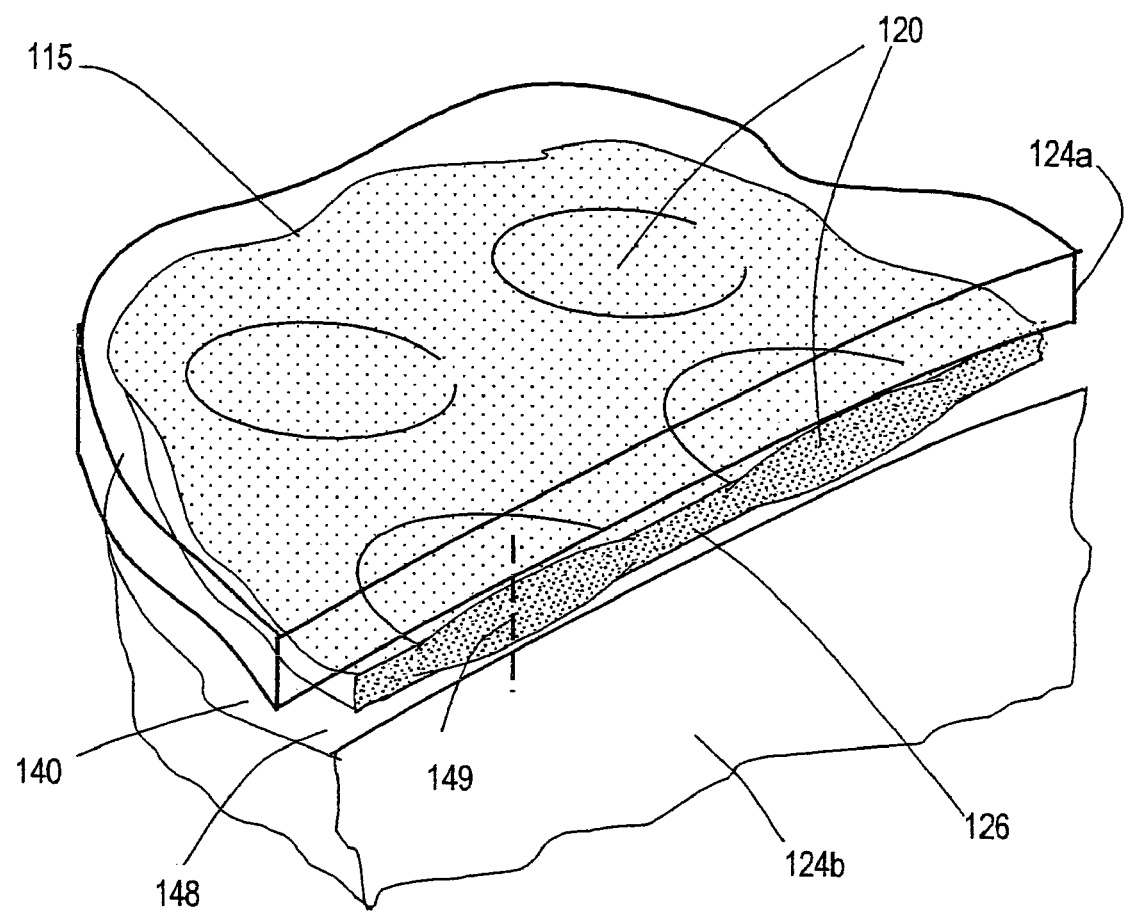
FIG. 6C is a sectional view of the interior phase portion of FIGS. 6A–6B in an interior space in a lens.
Figure 7:
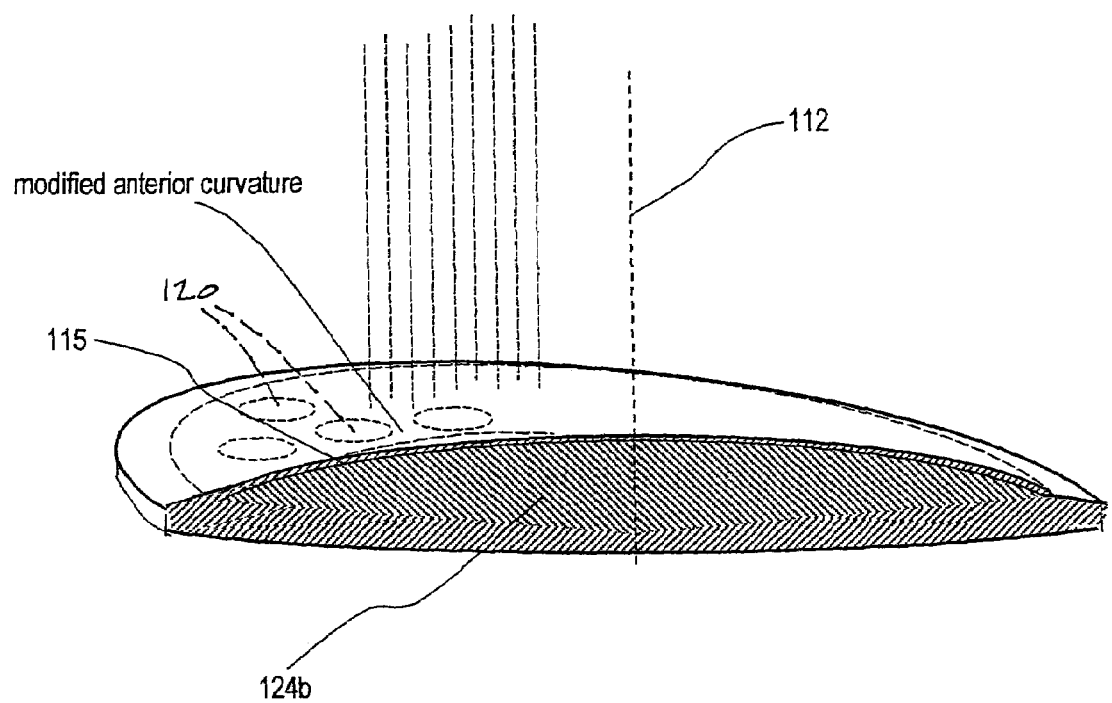
FIG. 7 is a sectional view of lens of FIG. 6C showing the shape modification of the anterior lens surface.

FIGS. 6A and 6B illustrate a method of manufacturing the interior phase 115 of the adaptive optic lens. The shape memory polymer displacement structures 120 can be molded in a memory shape of FIG. 6A, and then insert molded into intermediate media or phase portion 126, which in this case is an index matched polymer. Micromolding technology has developed easily allow molding on the scale of FIG. 6A. FIG. 6B next shows the assembly of FIG. 6A after the displacement structures 120 are being the compressed into its stable temporary shape. FIG. 6C shows the assembly of FIG. 6B within a space 148 between surface layer 124a and lens body portion 124b. The space 148 is also occupied by a fluid media 140 as described above. It can easily be understood how the displacement structures 120 will function as in the embodiment depicted in FIGS. 4, 5A and 5B. Referring again to FIG. 6C, the SMP structures 120 have a memory shape that defines a first greater lesser dimension about its axis 149 that is substantially orthogonal to the phase 115, with the second temporary shape defining a second lesser dimension about its axis 149. As can be understood from FIG. 4, the displacement structures 120 can be irradiated singularly or in any pattern to push axially (upwardly) on the thin resilient layer 124a to alter the optical characteristics of the lens wherein the intermediate phase portion 126 will float in space 148 within fluid 140. In another embodiment, the phase portion 126 between the actuators 120 can be a resilient open cell foam with an index matching fluid therein that migrates about the open cells. It can be easily understood from FIGS. 4, 6C and 7, the lens is suited for adjusting a selected local portion for higher order wavefront correction, astigmatisms and the like. Alternatively, all the displacement structures 120 can be adjusted for a global diopter change.

Figure 8:
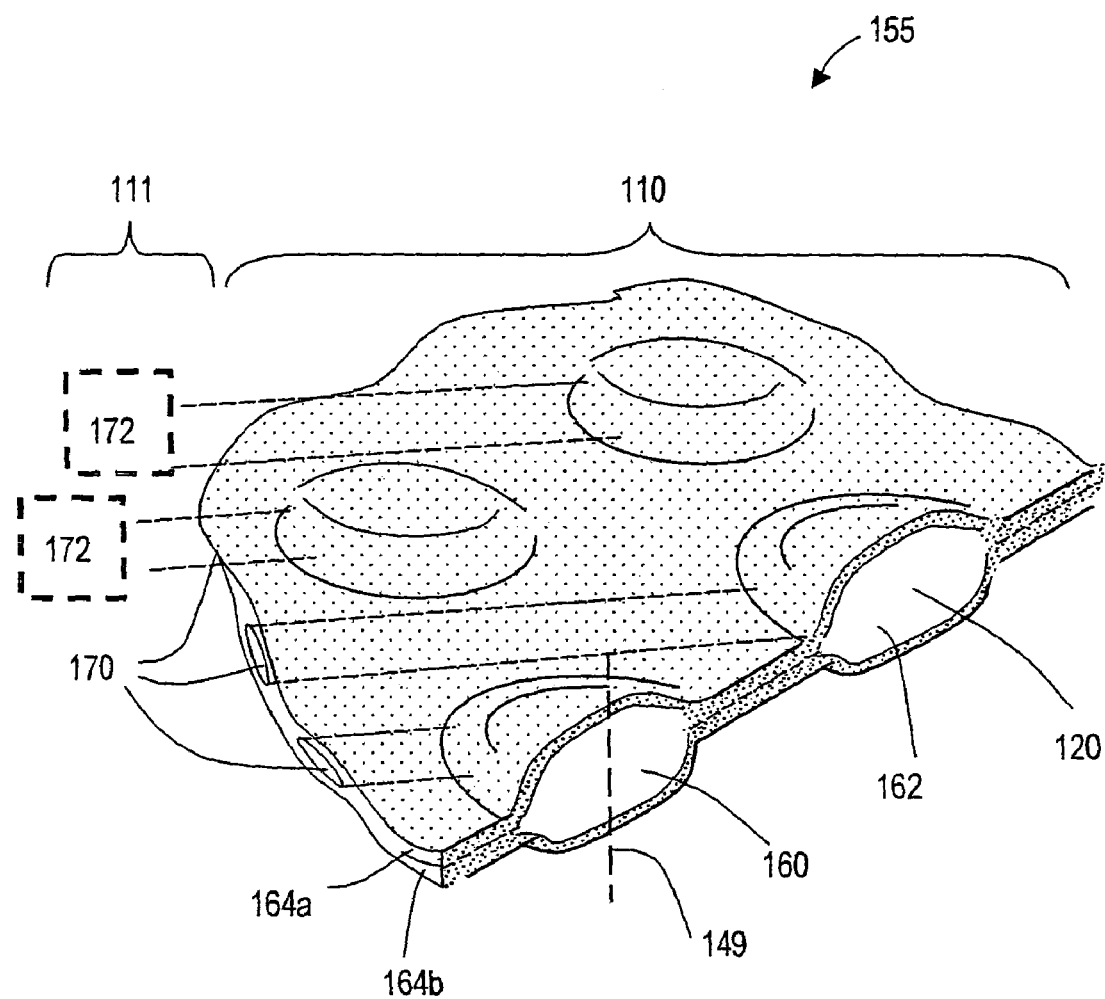
FIG. 8 is sectional view of a portion of an alternative interior phase of a lens that carries fluid-filled displacement structures capable of first and second shapes and volumes.

In another embodiment, shape memory polymers can be utilized in adaptive optic lens designs wherein the light energy is applied only in the non-optic portion 111 instead of the optic portion 110. In some lens designs, it may be preferable to use higher energy densities which are not transmitted to the retina. The non-optic portion 111 that is targeted can have a backing that prevents light transmission therethrough. FIG. 8 illustrates a small portion of an interior phase 155 that has displacement structures 120 that carry an index-matched fluid 160 within an interior space 162 in the displacement structures 120. FIG. 8 shows a manner of fabricating the assembly wherein first and second thin elastic layers 164a and 164b are bonded together to defines spaces 162 and channels 170 therein that extend to a non-optic portion 111 of the lens. In one example, the core layer 165 can be fabricated with spaces and flow channels by fabricating an open cell member and then using light to cure an infused polymer in all portions of the core layer 165 except the spaces and flow channels. To provide an actuatable displacement structure 120, the lens periphery 114 carries a plurality of shape memory polymer body portions 172 (collectively) that surrounds or are adjacent to the channels 170 that carries fluid media 160. It can be easily understood that light energy applied to a subpattern of SMP regions 172 about the periphery of the lens, with each SMP portion 172 is adapted to swell and impinge upon a flow channel to thereby push fluid media 160 into the displacement structure 120 to thereby deform the lens surface. It can be easily understood that the interior phase 155 of FIG. 8 can be assembled in a fluid-filled space exactly as in FIG. 6C to provide an adaptive optic. The system also can include a similar targetable SMP region adjacent a flow channel wherein the SMP is adapted to shrink or bend to different memory shape to draw fluid media 160 from the displacement structure 120 to reverse the shape change in the lens. Numerous variations are possible wherein irradiation of selected peripheral regions can alter polymer density, volume, shape or permeability to alter fluid pressure in a channel that communicates with a displacement structure 120.

Figure 9:
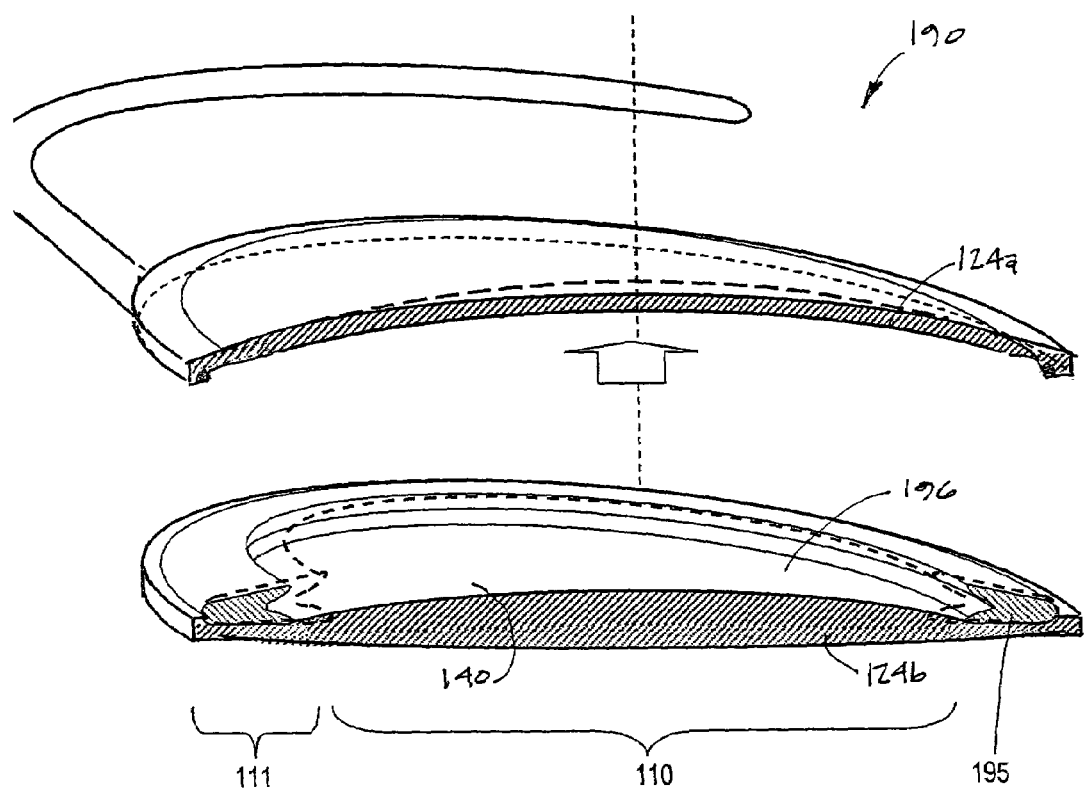
FIG. 9 is an exploded sectional view an alternative Type "A" lens with an annular SMP adaptive component at an interior periphery of the lens with a or gel fluid lens core.

Referring to FIG. 9, another IOL embodiment 190 is illustrated in exploded view wherein light energy again is applied only in the non-optic portion 111 instead of the optic portion 110. The embodiment of FIG. 9 comprises simplified adaptive optic that is designed only for spherical corrections and not high order aberration correction. The exemplary IOL of FIG. 9 has an annular SMP member 195 that can be moved from a temporary shape or porosity to a memory shape or porosity to achieve large diopter changes. The central portion or interior phase 196 of the lens can carry a fluid media 140 in an open chamber as described above, for example a silicone of a selected viscosity that may be gel-like. As in previous embodiments, the lens has non-permeable first and second surface layers 124a and 124b that envelope the interior phase 196. As can be seen in FIG. 9, it can be understood that light energy can be scanned and applied to the a annular SMP member 195 to move it toward its memory shape in phantom view to thereby apply pressure on the constrained media 140 in the interior phase 196 to alter the lens shape at its anterior surface from 122A to 122A' in phantom view.

Figure 10:
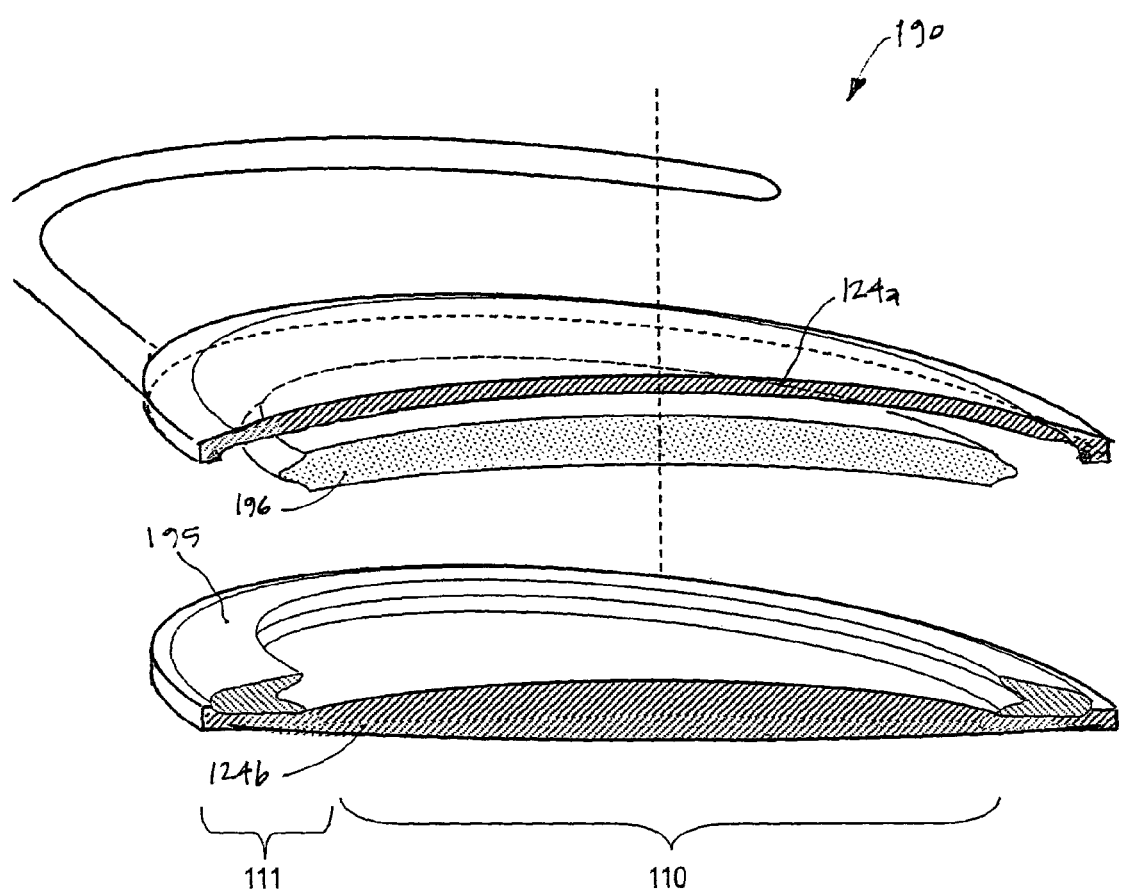
FIG. 10 is an exploded view of another lens embodiment similar to FIG. 9 wherein the annular SMP component is adapted to displace an interior fluid within a polymer matrix to cause shape change, wherein the combination of the fluid and the polymer comprises the actuator or displacement structure.
Figure 11:
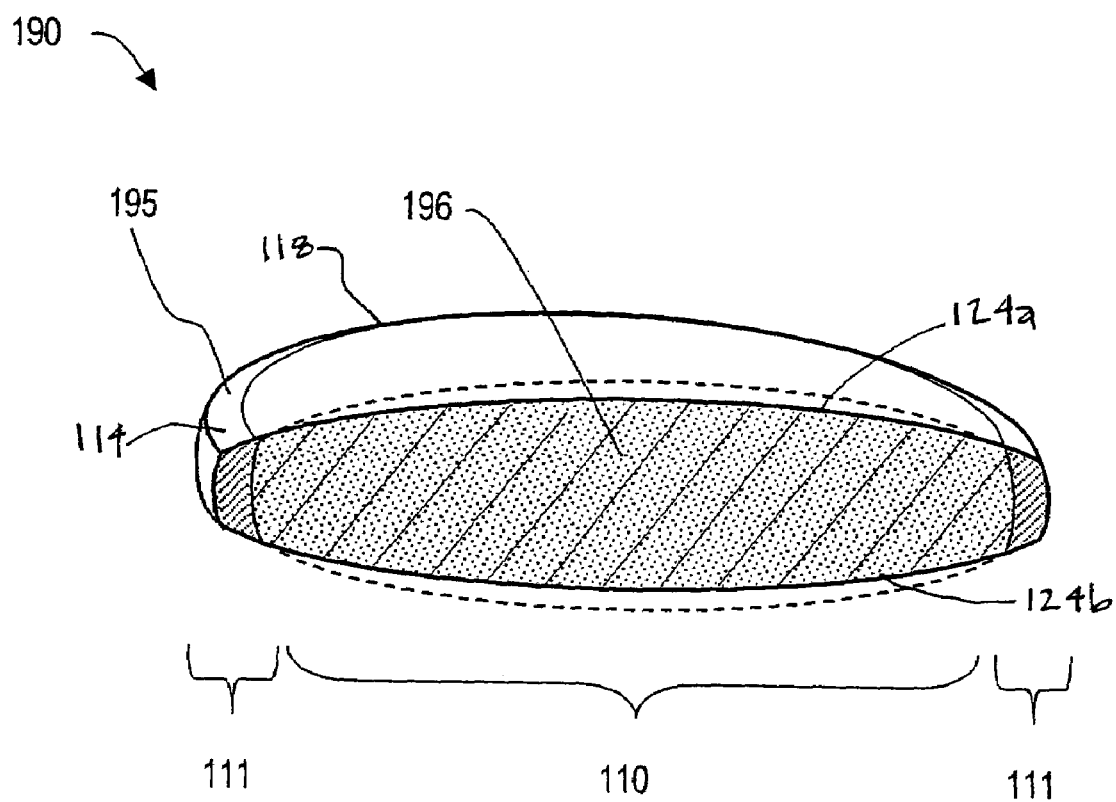
FIG. 11 is a sectional view of another lens similar to FIG. 9 wherein with an annular SMP component.

In another very similar embodiment as in FIG. 10, the central portion 196 can be a very low modulus index-matched polymer or an open cell SMP foam with a migrating fluid media 140 therein. In another similar embodiment as depicted in FIG. 11, the lens 190 has a central interior phase 196 of a very low modulus index-matched polymer or an open cell SMP foam with a migrating fluid media 140 therein. The annular SMP member 195 comprises the peripheral portion 114 of the lens body 118. This embodiment differs in that the non-permeable first and second surface layers 124a and 124b are very thin and preferably comprise a "surface modification" of the polymer of the a central interior phase 196. Such surface modifications of a polymers to provide an interior polymer portion that comprises a diffusion network while the micron thick surface layer is impermeable in known, as was described above (see. e.g., U.S. Pat. No. 5,235,003 to R. Ward et al.) This type of lens 190 would then be assembled of a limited set of components: the peripheral annular shape memory polymer portion 195 and the central interior phase 196 with its surface modification, and an optional fluid media 140 if the central phase 196 is porous polymer rather that a gel-like low modulus polymer.

2. Type "B" Soft Adaptive Optic System.

Figure 12:
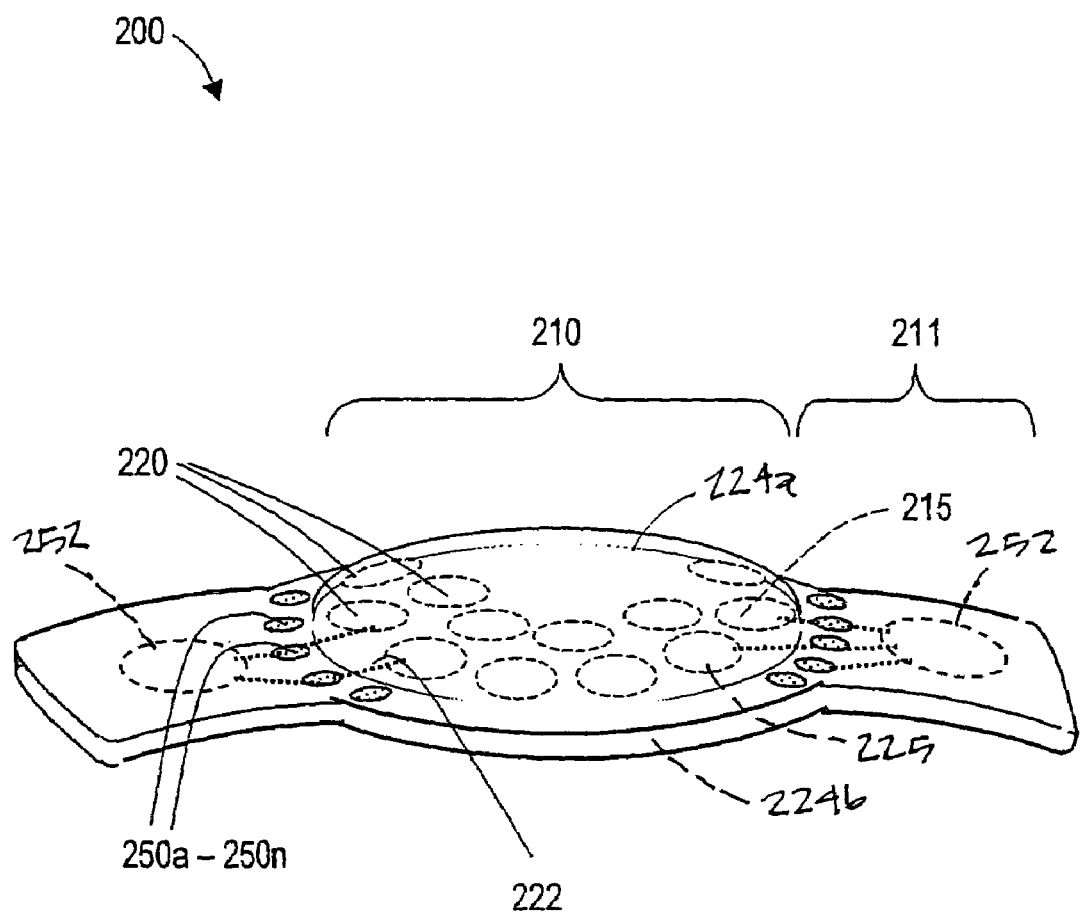
FIG. 12 is a schematic view of a Type "B" lens with an interior phase similar to that of FIGS. 8A–8C wherein the fluid-filled displacement structures are actuated by a sacrificial element in flow channels communicating with the displacement structures.

In another adaptive lens embodiment 200 depicted in FIG. 12, the lens again has an optic portion 210 and a non-optic portion 211. The lens has an interior form or phase 215 as depicted in FIGS. 6A–6C that is enveloped by anterior body portion or surface layer 224a and posterior body portion 224b. In this embodiment, the displacement structures 220 (collectively) operate as described previously to deform an anterior surface layer 224a. This embodiment differs in that shape memory polymers are in the same role to alter the volume of the fluid 225 in the displacement structures 220. In the exemplary embodiment of FIG. 12, the lens carries sacrificial elements 250a–250n in channels 222 (collectively) that individually communicate with space in each individual displacement structures 220a–220n.

In use, the lens is selected for a patient to have a positive power that exceeds the power indicated by biometry. When the lens 200 is implanted, the patient's intraocular pressure will cause interior pressure of the displacement structures 220 apply fluid pressure to sacrificial element, or the lens can be fabricated to provide an interior pressure in the displacement structures 220. After implantation, the sacrificial elements 250a–250n are individually targeted with light energy and sacrificed to thereby allow fluid flow through the channels 222 (collectively) to a potential space 252 in the non-optic portion 211 to receive the fluid 225. The sacrificial element can be a polymer that degrades under applied light energy, a polymer that becomes irreversibly (or reversibly) porous under applied light energy, a phase change polymeric material or any dissolvable metallic element known in the art.

It should be appreciated that lens can carry multiple layers of adaptive optic structures in fluid permeable planes for flexing the lens surface. The lens can carry adaptive optic structures that operate in a single lens that operate to apply forces both parallel to the optical axis and for applying forces orthogonal to the optical axis for flexing the lens surface. The lens can layered adaptive optic structures for flexing the lens surface in opposing directions to allow for very fine adjustments or reversible adjustments. In one preferred embodiment, the adaptive optic structures can be spaced apart with individual addresses or coordinates to cooperate with a scanned light source, wherein the number of discrete adaptive optic features can range in number from as few as about 100 to as high as several million. In another preferred embodiment, a layer of material in the lens may be "adaptive" in any location thereof to allow targeting of any location or region thereof.

In another embodiment, the intraocular lens can be combined with a wavefront sensing system (e.g. a Shack Hartman system) to allow computer-controlled correction of aberrations in the lens.

Figure 13:
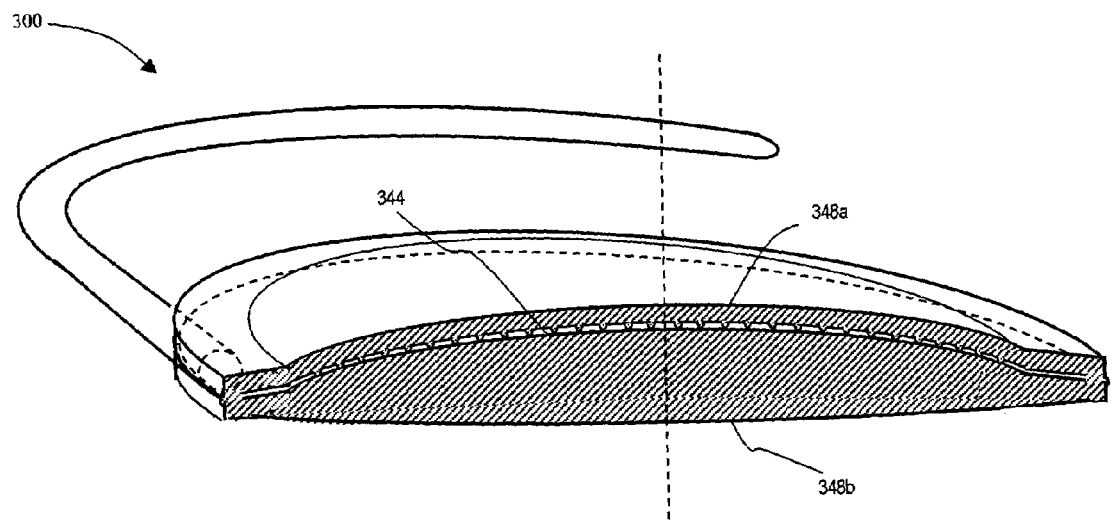
FIG. 13 is a sectional view of another lens similar to FIG. 4.
Figure 14:
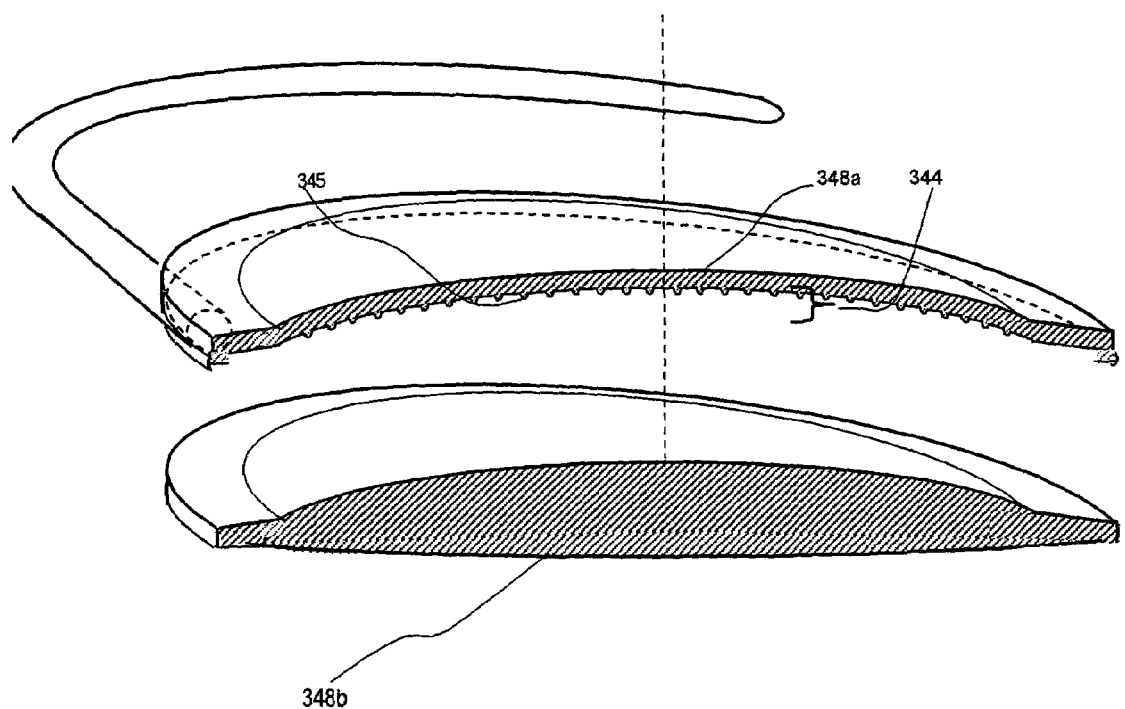
FIG. 14 is an exploded view of the lens of FIG. 13 showing a method of making the lens.

Referring now to FIGS. 13 and 14, an exemplary lens 300 with its adaptive structure or interior phase is shown to illustrate the manner of making an adaptive lens for localized surface curvature change. The "adaptive" surface relief elements 345 comprise a shape memory polymer that is molded into a unitary surface layer or body 348a that can be coupled a molded base or body surface 348b. In a first dimensional configuration or shape profile of each adaptive structure 344, the lens is provided with a first anterior curvature AC. As can be understood from FIGS. 4–5B, the adaptive elements 345 of FIGS. 13–14 each have an address that is targetable. The method of making the lens consists of molding the first and second body portions 348a and 348b and thereafter bonding together these body portions together with an index-matched fluid. Again, the method of the invention utilizes energy from an external light source for example in a scanned beam, as directed by the computer controller to irradiate each address. In this exemplary embodiment, the light source (and controller and scanner) with a selected wavelength, scan rate, power level, pulse duration, dwell time, beam profile (also possible repetition rate) is scanned to irradiate the selected locations to alter the axial or cross-axial dimension of the individual adaptive structures. By this means, it can easily be understood how the adaptive structure can be used to alter a selected portion of the lens surface from its initial anterior curvature to a modified anterior curvature. Of particular interest, as the adaptive structure alters the lens curvature, the matching index fluid 140 self-directs itself to move or flow into the newly shaped volume of the interior phase or plane.

Those skilled in the art will appreciate that the exemplary embodiments and descriptions thereof are merely illustrative of the invention as a whole, and that variations in controlling the of intervals of energy delivery may be made within the spirit and scope of the invention. Specific features of the invention may be shown in some figures and not in others, and this is for convenience only and any feature may be combined with another in accordance with the invention. While the principles of the invention have been made clear in the exemplary embodiments, it will be obvious to those skilled in the art that modifications of the structure, arrangement, proportions, elements, and materials may be utilized in the practice of the invention, and otherwise, which are particularly adapted to specific environments and operative requirements without departing from the principles of the invention. The appended claims are intended to cover and embrace any and all such modifications, with the limits only of the true purview, spirit and scope of the invention.

What is claimed is:

1. A method of making an ophthalmic lens comprising the steps of sealably assembling anterior and posterior lens body portions about an interior phase that carries and a fixed pattern of actuatable displacement structures for deforming the lens surface to alter an optical parameter of the lens, the interior phase further comprising an index-matched fluid layer about the displacement structures, wherein the displacement structures define a scale that allows for correction of higher order aberrations.

2. A lens for spherical or higher order aberration correction in a human vision treatment, comprising a lens body defining an optical axis, a lens having an interior phase extending transverse to the optical axis that carries and a fixed pattern of actuatable displacement structures for deforming a lens surface to alter an optical parameter of the lens, wherein the displacement structures define a scale that allows for correcting higher order aberrations.

3. A lens as in claim 2, wherein the one lens surface is resilient to permit a shape change in response to actuation of the displacement structure.

4. A lens as in claim 2, wherein both anterior and posterior lens surfaces are resilient.

5. A lens as in claim 2 wherein the displacement structures are arranged over in concentric circles in the interior phase.

6. A lens as in claim 2, wherein the displacement structures changes a selected functional parameter in response to energy applied to a cooperating lens component from a light source, the functional parameter selected from the class consisting of volume, shape, porosity, density, internal pressure and interior fluid pressure.

7. A lens as in claim 6, wherein the cooperating lens component is a photo-modifiable polymer.

8. A lens as in claim 6, wherein the cooperating lens component is a hydrogel which swells or contracts.

9. A lens as in claim 6, wherein the displacement structure is alterable in volume in response to the applied energy to media adjacent said fluid.

10. A lens as in claim 6 wherein the cooperating lens component is stably compressed or extended to store energy which is released in response to the applied energy.

11. A lens as in claim 6, where cooperating lens component carries a chromophore which selectively absorbs a predetermined light wavelength.

12. A method for adjusting an optical characteristic of vision correction lens, said method comprising applying energy from a remote energy source to a cooperating lens component wherein the cooperating lens component alters a parameter of a displacement element in the lens body of the lens, wherein the displacement element adjusts an optical characteristic of the lens at a plurality of locations sufficient to correct higher order aberrations.

13. A method as in claim 12, wherein the applying energy step utilizes light energy.

14. A method as in claim 12, wherein the applying energy step scans a laser beam to irradiate the cooperating lens component.

15. A method as in claim 12, wherein the altering step alters a volume parameter of a displacement element.

16. A method as in claim 12, wherein the altering step alters a shape parameter of a displacement element.

17. A method as in claim 12, wherein the altering step alters a porosity parameter of a displacement element.

18. A method as in claim 12, wherein the altering step alters a density parameter of a displacement element.

19. A method as in claim 12, wherein the altering step alters an internal pressure parameter of a displacement element.

20. A method as in claim 12, wherein the altering step alters an interior fluid pressure parameter within a displacement element.

* * * * *